(12) United States Patent
Hewitt

(10) Patent No.: US 10,420,671 B2
(45) Date of Patent: Sep. 24, 2019

(54) OSTOMY POUCH ASSEMBLY

(71) Applicant: Pelican Healthcare Limited, Cardiff (GB)

(72) Inventor: Aaron Hewitt, Comber (GB)

(73) Assignee: Pelican Healthcare Limited, Cardiff (GB)

( * ) Notice: Subject to any disclaimer, the term of this patent is extended or adjusted under 35 U.S.C. 154(b) by 892 days.

(21) Appl. No.: 14/760,675

(22) PCT Filed: Jan. 10, 2014

(86) PCT No.: PCT/GB2014/050074
§ 371 (c)(1),
(2) Date: Jul. 13, 2015

(87) PCT Pub. No.: WO2014/108700
PCT Pub. Date: Jul. 17, 2014

(65) Prior Publication Data
US 2015/0351952 A1    Dec. 10, 2015

(30) Foreign Application Priority Data
Jan. 14, 2013 (GB) .................................. 1300564.0

(51) Int. Cl.
*A61F 5/443* (2006.01)
*B29C 65/40* (2006.01)
(Continued)

(52) U.S. Cl.
CPC .............. *A61F 5/443* (2013.01); *A61F 5/445* (2013.01); *B29C 65/02* (2013.01); *B29C 65/40* (2013.01);
(Continued)

(58) Field of Classification Search
CPC combination set(s) only.
See application file for complete search history.

(56) References Cited

U.S. PATENT DOCUMENTS

| 4,213,458 A |   | 7/1980 | Nolan et al. |
|---|---|---|---|
| 5,722,965 A | * | 3/1998 | Kuczynski ............. A61F 5/443 604/338 |

(Continued)

FOREIGN PATENT DOCUMENTS

| EP | 1378219 A2 | 1/2004 |
|---|---|---|
| GB | 2290713 A | 1/1996 |

(Continued)

OTHER PUBLICATIONS

International Search Report in Priority International Application No. PCT/GB2014/050074, dated Apr. 3, 2014.

(Continued)

*Primary Examiner* — Tatyana Zalukaeva
*Assistant Examiner* — Guy K Townsend
(74) *Attorney, Agent, or Firm* — Troutman Sanders LLP; Ryan A. Schneider

(57) ABSTRACT

An ostomy pouch assembly (1) comprises a receptacle (2) for receiving material from a stoma of a person, and a mounting plate (4) for securing the receptacle to a person's body. The mounting plate includes a first layer (10) with an outer surface that is configured to be bonded to a person's skin and an inner surface. An intermediate layer (12) is located between the inner surface of the first layer (10) and the receptacle (2). A stress displacement or bonding layer (16) is located between the intermediate layer (12) and the receptacle (2) for bonding the mounting plate (4) to the receptacle (2). The region of bonding securement between the bonding layer (16) and the intermediate layer (12) has a first peripheral edge (20), and the region of bonding securement between the bonding layer and the receptacle has a second peripheral edge (26) that is located inwardly of the first peripheral edge (20).

13 Claims, 4 Drawing Sheets

(51) Int. Cl.
  *B29C 65/00* (2006.01)
  *B29C 65/02* (2006.01)
  *A61F 5/445* (2006.01)
  *A61F 5/448* (2006.01)
  *B29L 31/00* (2006.01)
  *B29K 701/12* (2006.01)

(52) U.S. Cl.
  CPC .. *B29C 66/7315* (2013.01); *A61F 2005/4483* (2013.01); *B29K 2701/12* (2013.01); *B29L 2031/7148* (2013.01)

(56) References Cited

U.S. PATENT DOCUMENTS

| | | | | |
|---|---|---|---|---|
| 5,938,647 | A * | 8/1999 | Smith | A61F 5/445 128/DIG. 24 |
| 6,939,936 | B2 * | 9/2005 | Wang | A61L 15/585 156/331.6 |
| 2004/0006320 | A1 * | 1/2004 | Buglino | A61F 5/443 604/344 |
| 2004/0065232 | A1 * | 4/2004 | Lykke | A61L 15/585 106/680 |
| 2004/0133175 | A1 * | 7/2004 | Hagedorn-Olsen | A61F 5/448 604/332 |
| 2005/0084634 | A1 * | 4/2005 | Giori | A61F 5/448 428/35.2 |
| 2005/0136266 | A1 * | 6/2005 | Zhou | A61L 15/58 428/447 |
| 2005/0143696 | A1 * | 6/2005 | Pedersen | A61F 5/441 604/332 |
| 2006/0177489 | A1 * | 8/2006 | Massouda | A61L 15/28 424/443 |
| 2006/0177490 | A1 * | 8/2006 | Massouda | A61K 9/2027 424/443 |
| 2006/0184145 | A1 * | 8/2006 | Ciok | A61F 5/443 604/338 |
| 2006/0195053 | A1 * | 8/2006 | Oelund | A61F 5/443 602/43 |
| 2007/0027434 | A1 * | 2/2007 | Pedersen | A61F 5/441 604/333 |
| 2007/0060855 | A1 * | 3/2007 | Leung | A61L 15/225 602/41 |
| 2007/0179461 | A1 * | 8/2007 | Sambasivam | A61L 15/58 604/336 |
| 2007/0185464 | A1 * | 8/2007 | Fattman | A61F 5/443 604/336 |
| 2007/0261789 | A1 * | 11/2007 | Giori | A61F 5/448 156/308.4 |
| 2009/0306571 | A1 * | 12/2009 | Lam | A61L 15/585 602/56 |
| 2010/0030167 | A1 * | 2/2010 | Thirstrup | A61F 5/445 604/318 |
| 2010/0191204 | A1 * | 7/2010 | Bach | A61F 5/443 604/344 |
| 2011/0054425 | A1 | 3/2011 | Smith et al. | |
| 2011/0213321 | A1 * | 9/2011 | Fattman | A61F 5/448 604/344 |
| 2011/0230850 | A1 * | 9/2011 | Stroebech | A61F 5/443 604/344 |
| 2013/0274696 | A1 * | 10/2013 | Lam | A61F 5/443 604/332 |
| 2015/0018790 | A1 * | 1/2015 | Lam | A61F 5/4404 604/344 |
| 2015/0351952 | A1 * | 12/2015 | Hewitt | A61F 5/445 604/336 |
| 2016/0143768 | A1 * | 5/2016 | Stroebech | A61L 24/06 604/344 |

FOREIGN PATENT DOCUMENTS

GB  2418861 A  4/2006
WO  2005041827 A2  5/2005

OTHER PUBLICATIONS

Search Report in Priority GB Application No. GB1300564.0, dated Apr. 17, 2013.

* cited by examiner

OSTOMY POUCH ASSEMBLY

CROSS-REFERENCE TO RELATED APPLICATIONS

This application is a US National Stage of International Application No. PCT/GB2014/050074 filed 10 Jan. 2014, which claims the benefit of GB 1300564.0 filed 14 Jan. 2013, each herein fully incorporated by reference.

The present invention relates to an ostomy pouch assembly and in particular to an ostomy pouch assembly having an improved bonding between the ostomy bag and the ostomy mounting plate.

An ostomy pouch is a medical prosthetic that provides a means for collecting waste diverted from a biological system of a patient's body such as the colon, ileum, or urinary system. The ostomy pouch is mounted on the body at the site of a stoma, or opening, from which the bodily waste products are to be received by the pouch.

An ostomy pouch assembly typically consists of a collection pouch and a mounting for attaching the collection pouch to a patient's, or 'ostomate's', body. The collection pouch is attached to the mounting plate to form an air and liquid tight seal. It has been known for such appliances to be attached to a patient mechanically. However, a preferable means of attachment is to bond the mounting plate to the patient's body by means of an adhesive as such bonding provides a more efficient seal between the patient's body and the mounting plate. The mounting plate may include a layer of material suitable for attachment to the skin of the user of the appliance.

It is desirable for the mounting plate to include a foam comfort layer to provide a soft feel, flexible interface with the patient's skin. The foam layer is typically located between a hydrocolloid layer which adheres to the patient's skin and the bag. Where a rigid plastic substrate such as a convex dome is incorporated into the mounting plate, the foam comfort layer may be adhered to the plastic member, which in turn may then be adhered to the bag. However, where no such member is included, such as in planar foam backed discs, it has been found that there are difficulties in adhering a foam intermediate layer directly to the plastic film the ostomy bag. A particular issue is that direct adhesion provides a stress riser at the point of bonding which can lead to the foam layer peeling or tearing, or the bond otherwise failing under the application of a tensile or shear force, Such a force may occur, for example, when the surface of the hydrocolloid disc has been attached to a user's body and the bag is pulled, dragged, or otherwise moved. This peeling is particularly noticed where an ostomy bag is bonded such as by thermal welding directly to a foam layer. Damage of this type causes the pouch to lose its sealing integrity, leading to leakage of waste products. This will be inconvenient and distressing to the user, as well as being a potential source of infection.

It is therefore desirable to provide an improved ostomy pouch assembly which addresses the above described problems and/or which offers improvements generally.

According to the present invention there is provided an ostomy pouch assembly as described in the accompanying claims. According to the present invention there is also provided a method of forming an ostomy pouch assembly as described in the accompanying claims.

In an embodiment of the invention there is provided an ostomy pouch assembly comprising a receptacle for receiving material from a stoma of a person; a mounting plate for securing the receptacle to a person's body, the mounting plate including a first layer having an outer surface configured to be bonded to a person's skin and an inner surface, and an intermediate layer located between the inner surface of the first layer and the receptacle; and a stress displacement or bonding layer located between the intermediate layer and the receptacle for bonding the mounting plate to the receptacle. The region of bonding securement between the bonding layer and the intermediate layer has a first peripheral edge, and the region of bonding securement between the bonding layer and the receptacle has a second peripheral edge that is located inwardly of the first peripheral edge. The receptacle is preferably a bag formed from a flexible nonporous material.

By locating the outer peripheral edge of the region of bonding securement between the bonding layer and the receptacle inwardly of the peripheral edge of the region of bonding securement between the bonding layer and the intermediate layer, the stresses acting to part the bonding layer and the bag act at a distance inwardly of the outer peripheral edge of the bonding region between the bonding layer and the support layer. In this way the stress is moved inwardly away from this edge contact between the bonding layer and the intermediate foam support layer, and the risk of tearing of the surface of the support layer is significantly mitigated.

The first layer is preferably skin contact layer such as a hydrocolloid layer configured to be adhered to a person's skin, and the intermediate or support layer is a foam material. The intermediate layer is preferably adhered directly to the first layer.

Preferably the first and intermediate layers are planar members. They may comprise a common peripheral edge that is located outwardly of the first and second peripheral edges.

Preferably an aperture extends through both the first and intermediate layers defining a stoma port, and the stoma port is located inwardly of both the first and second peripheral edges.

The bonding layer is preferably substantially annular having an inner edge and an outer peripheral edge. The outer peripheral edge defines the first peripheral edge of bonding region. The second peripheral edge of the bonding region is located between the first peripheral edge and the inner peripheral edge of the bonding layer. The annular form of the bonding layer provides a complete seal about the stoma port while minimising material usage and maintaining maximum flexibility of the mounting plate which would otherwise be limited if the more rigid thermoplastic bonding layer were to extend radially inwardly to a position proximate the stoma port.

A portion of the bag is preferably bonded to the intermediate layer inwardly of the inner peripheral edge of the bonding layer. This prevents egress of material from the stoma between the receptacle and the intermediate layer in the region between the stoma port and the bonding layer to increase the efficacy of the seal between the bag and the mounting plate. Any direct tearing or peeling force is experienced at the bonding region between the bonding layer and the bag, and as such thermal welding is sufficient to securely bond the bag to the intermediate layer in the region inside the bonding layer.

An aperture is defined in the bag which is aligned with the aperture extending through the first and intermediate layers to form part of the stoma port. The aperture defines an inner edge and the bag is bonded directly to the intermediate layer between the inner peripheral edge of the bonding layer and the inner edge defined by the aperture in the bag.

In another aspect of the invention there is provided a method of forming an ostomy pouch assembly comprising:

providing a receptacle for receiving material from a stoma of a person, and a mounting plate for securing the receptacle to a person's body, the mounting plate including a first layer having an outer surface configured to be bonded to a person's skin and an inner surface, and an intermediate layer located between the inner surface of the first layer and the receptacle;

applying a bonding layer to the intermediate layer on the opposite side the first layer to define a region of bonding securement between the bonding layer and the intermediate layer having a first peripheral edge; and bonding the receptacle to the bonding layer on the opposite side to the intermediate layer to define a region of bonding securement between the bonding layer and the receptacle that has a second peripheral edge located inwardly of the first peripheral edge.

The bonding layer is preferably formed from a thermoplastic material and the step of applying the bonding later to the intermediate layer includes melting the thermoplastic material and applying the melted thermoplastic to the surface of the intermediate layer to form a layer of thermoplastic bonded to the intermediate layer and having a periphery defining the first peripheral edge.

The receptacle is preferably bonded to the bonding layer by thermal welding such that the second peripheral edge defined by the outermost bonding securement between the receptacle and the bonding layer is inwardly of the first peripheral edge.

The bonding layer is preferably formed on the intermediate layer in a substantially annular form.

The bonding layer preferably has an inner edge and an outer peripheral edge which is the first peripheral edge. The bag is bonded to the bonding layer such that the second peripheral edge is located between the first peripheral edge and the inner peripheral edge of the bonding layer.

An aperture may be defined in the bag which is aligned with the aperture extending through the first and intermediate layers to form part of the stoma port, the aperture defines an inner edge and wherein the bag is thermally welded directly to the intermediate layer between the inner peripheral edge of the bonding layer and the inner edge defined by the aperture in the bag.

The step of thermally welding the bag to the intermediate layer is preferably conducted simultaneously with the step of thermally welding the bag to the bonding layer in the same thermal welding operation thereby improving the efficiency of the manufacturing process.

Preferably the first and intermediate layers are substantially disc shaped and the second peripheral edge is located radially inwardly of the first peripheral edge.

The present invention will now be described by way of example only with reference to the following illustrative figures in which.

Figure 1:
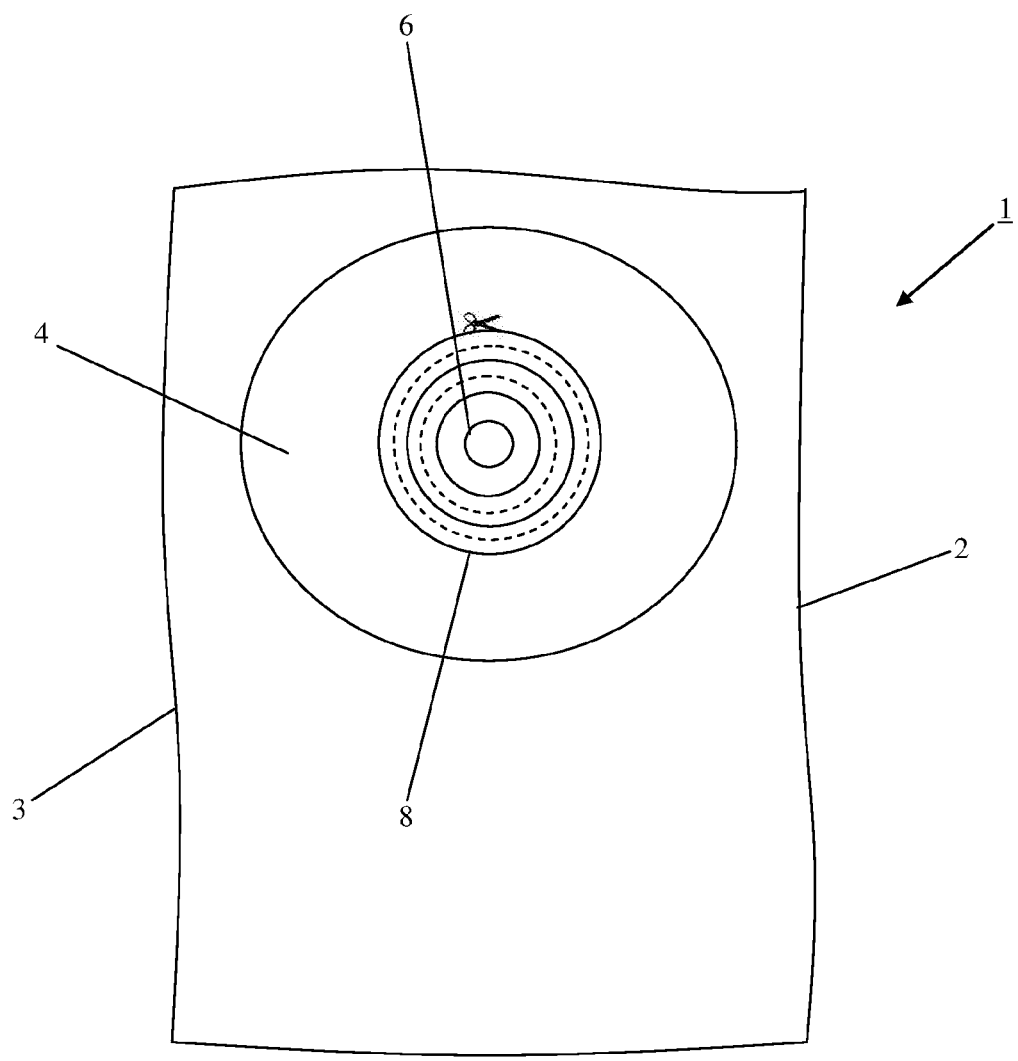
FIG. 1 shows an ostomy pouch according to an embodiment of the invention.

Referring to FIG. 1, an ostomy pouch assembly 1 includes a bag 2 and an ostomy mounting plate 4. The bag 2 is formed from two sheets of a flexible plastic material, preferably medical plastic film, which are bonded around their peripheral edges 3 to form a sealed enclosure. A double-layered cloth covering (not shown) may also be provided to cover and protect and obscure it from view in use.

The bag 2 provides a receptacle for receiving material from the stoma of a patient. In order to function in use the bag must be held securely relative to the stoma and a seal must be provide to prevent the release of material from the bag. The mounting plate 4 is provided to mount the bag 2 to the body of a patient. The mounting plate 4 includes an aperture 6 which aligns with a corresponding aperture formed in the bag 2 which define a stoma port for receiving the patient's stoma. The mounting plate 4 is provided with concentric circular guidelines 8 to allow the user to cut the plate 4 to increase the size of the aperture 6 to correspond to and fit the size of the stoma.

Figure 2A:
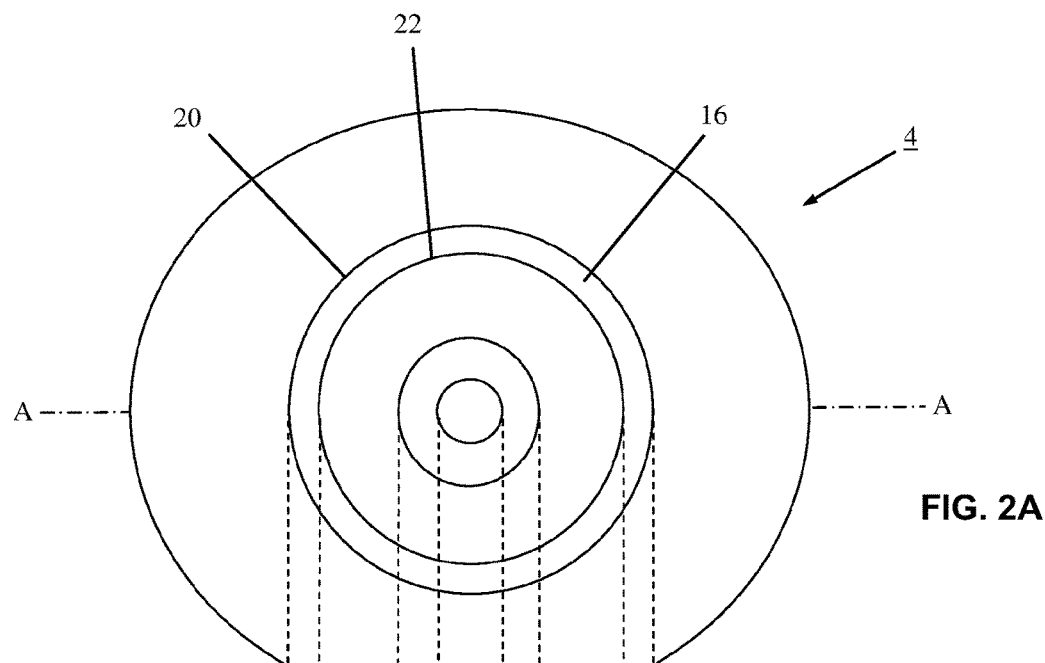
FIG. 2A shows a plan view of the ostomy pouch of FIG. 1.
Figure 2B:
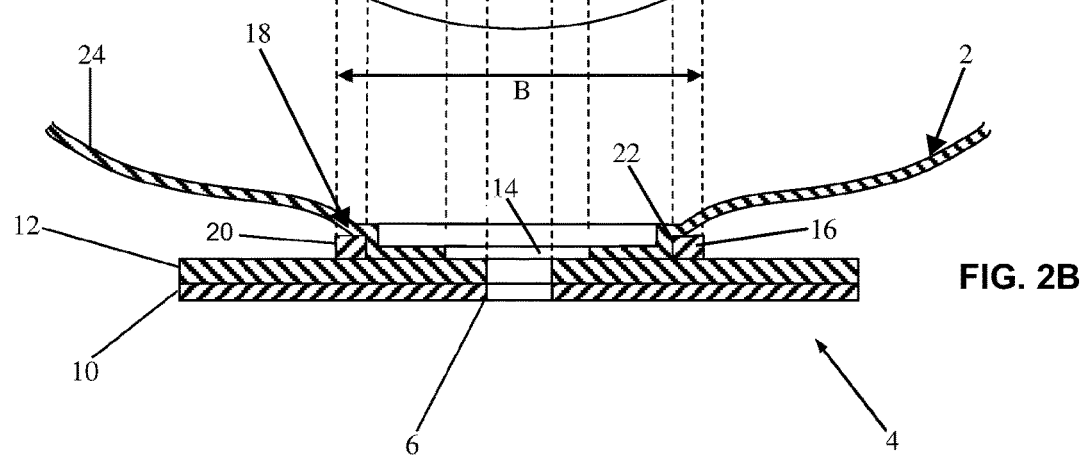
FIG. 2B shows a section view of the ostomy pouch of FIG. 1, with the alignment of the layer edges of the plan view and the section view indicated by dashed lines.

In the embodiment of FIGS. 2A and B, which shows a plan view of the mounting plate 4 together with a section view through the A-A, the mounting plate 4 comprises a first outer contact layer 10 which in use faces outwardly towards the patient's body and is configured to engage and bond to the patient's skin. It should be noted that in FIGS. 2A and B and the subsequent figures the represented thicknesses of the various layers have been exaggerated for illustrative purposes. The first outer contact layer 10 is formed of a hydrocolloid material with the outer surface comprising an adhesive for securing the mounting plate 4 to a patient's skin on contact. A release layer of this film (not shown) is provided which is peeled off the hydrocolloid material before use of the appliance.

The mounting plate 4 also includes a second intermediate support layer 12 which is located on the opposing side of the contact layer to the skin contact adhesive between the contact layer 10 and the bag 2, which in use is inwardly of the first contact layer in the direction away from patient's body. The second intermediate support layer 12 is formed from a closed cell foam material such as polyethylene foam, which supports the contact layer 10 as well as providing a cushioning effect to the disc to minimise discomfort to the wearer. The support layer 12 and the contact layer 10 are both substantially disc shaped, which in the embodiment shown comprises a planar semi-elliptical shape. In other embodiments the support layer 12 and contact layer 10 may be any other suitable shape. The contact layer 10 and support layer 12 are preferably the same size and shape and are adhered to each other to their outer edges. The aperture 6 is formed in and extends through and is defined by the radially inner edges of the both the contact layer 10 and the support layer 12.

The bag 2 includes an aperture 14 which aligns with the aperture 6 of the mounting plate 4 to form part of the stoma port. The aperture 14 may have a diameter greater than the aperture 6 to allow the bag 2 to be more easily aligned with the mounting plate 4 without requiring accurate alignment of two equally sized apertures. In order to function properly the bag must be secured relative to the mounting plate in such a way that a seal is formed between the bag and the plate to prevent leakage of material from the stoma. In trials it was attempted to thermally weld the bag 2 directly to the intermediate support layer 12. However, it was identified that this direct thermal welding resulted in tearing of the foam material of the support layer 12 when a tensile or shear force was applied pulling the bag 2 and mounting plate 4 is opposing directions. In particular it was noted that the forces were concentrated at the periphery of the bond between the bag 2 and the support layer 12 leading to a stress riser which caused tearing of the support later and/or the bag leading to failure of the bond and the seal between the two surfaces.

An intermediate stress-displacement element is provided between the bag 2 and the mounting plate 4 in the form of a bonding layer 16. The bonding layer 16 is an annular plastic layer which is arranged substantially concentric to the stoma port and has a diameter greater than the stoma port, greater than the largest permitted guide diameter to which the stoma port may be cut, and less than the diameter of the mounting plate 4 such that it is located inwardly outer peripheral edge of the mounting plate and outwardly of the inner peripheral edge defining the stoma port. The bonding layer 16 is a continuous uninterrupted ring.

The bonding layer 16 is formed by applying an annular layer of hot melt thermoplastic to the surface of the foam support layer 12. The hot melt application of the thermoplastic bonding layer 16 to the foam surface of the support layer 12 adheres the bonding layer 16 to the support layer 12. The bonding layer 16 is then allowed to cool and set, hardening to a solid flexible form. The annular bonding layer 16 when formed includes a substantially flat upper surface 18, an outer peripheral edge 20 defining a diameter B and a peripheral inner edge 22. The bonding layer 16 is bonded to the support layer 12 across its entire lower surface defining an annular bonding region between the bonding layer 16 and the support layer 12 that extends to the outer peripheral edge 20 from the inner peripheral edge 22.

When the bonding layer 16 has set a first film 24 of the two plastic films of the bag 2 which includes the aperture 14 is brought into engagement with the bonding layer 16 and the support layer 12 and the aperture 14 is aligned with the aperture 6. This step may be performed before the first film 24 is bonded to the second film to form the bag 2. As such, reference in the claims to the bag and to bonding the bonding layer to the bag or a part of the bag may mean the fully assembled bag or a part of the bag such as the plastic film 24 forming part of the bag prior to or after the first film 24 being secured to the second film either in whole or in part. The film 24 is then thermally welded to both the bonding layer 16 and the support layer 12 simultaneously in a single thermal welding operation.

Figure 3A:
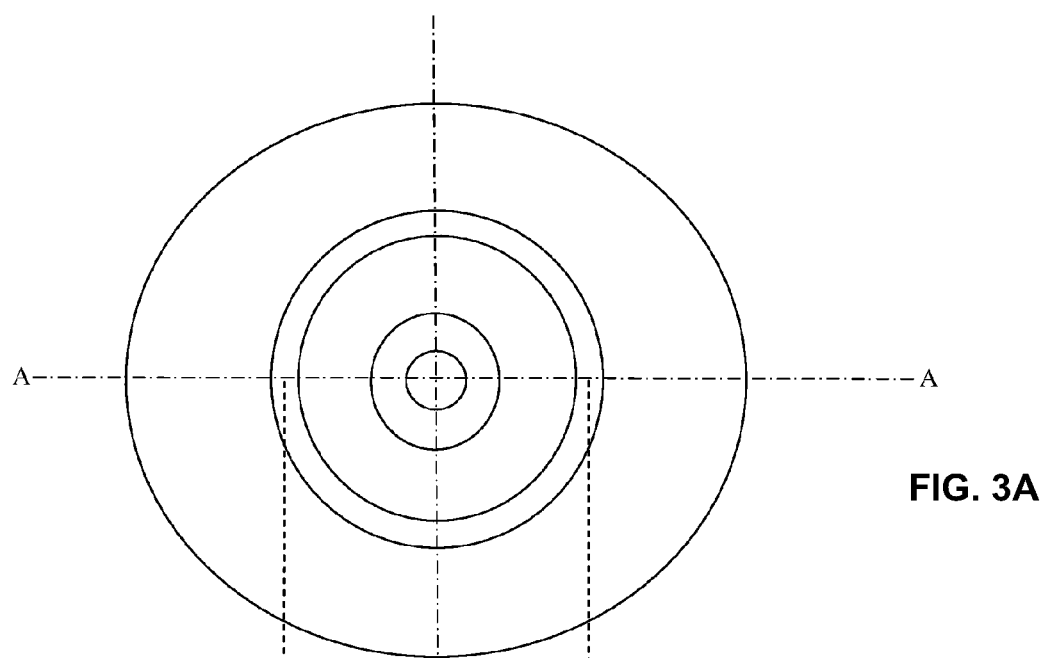
FIG. 3A shows a plan view of the ostomy pouch of FIG. 1.
Figure 3B:
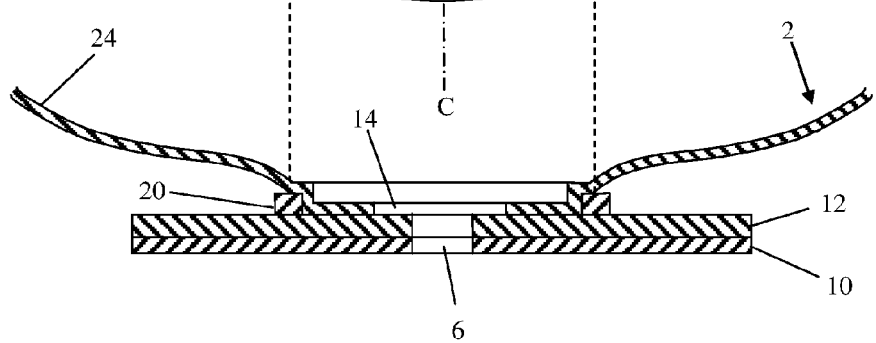
FIG. 3B shows a section view of the ostomy pouch of FIG. 1, with the alignment of the outer edge of the bonding region between the bonding layer and the intermediate support layer of the plan view and the section view indicated by dashed lines.
Figure 4:
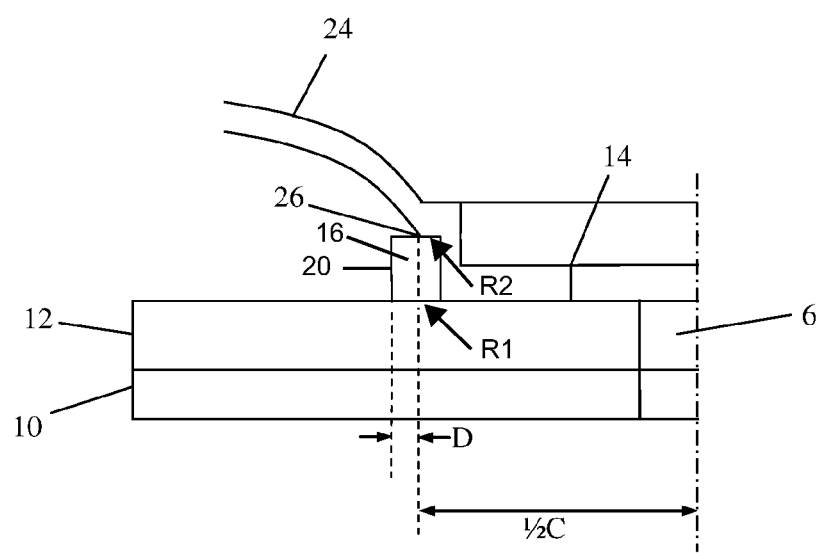
FIG. 4 is an enlarged section view illustrating the peripheral boundaries of the bonding securement regions.

The film 24 of the bag 2 is bonded to the bonding layer 16 in an annular bonding region having a diameter C which is less that the outer diameter B of the bonding layer 16, as shown in FIGS. 3A and B. As shown in FIG. 4 the outer peripheral edge 26 of the region R2 of bonding securement between the film 24 and the bonding layer 16 is located a distance D radially inwards of the outer peripheral edge 20 of the bonding region 16. Radially inwards of the inner edge 22 of the bonding layer 16 the film 24 is bonded by thermal welding directly to the support layer 12 between the inner edge 22 of the bonding layer 16 and the inner edge of the film 24 defining the aperture 14. In this way, when a tensile force is applied pulling the bag 2 away from the mounting plate 4, the stresses acting to part the bonding layer 16 and the bag 2 act at a distance D inwardly of the outer peripheral edge of the bonding region R1 spanning the contact surface of the bonding layer 16 and the support layer 12. As such, the stress is moved inwardly away from this edge contact between the bonding layer 16 and the foam support layer 12. The stress is therefore more evenly distributed to the support layer 12 across the base of the bonding layer 16 through the entire bonding region rather than at a point of elevated stress at the bonding intersection between the outer peripheral edge 20 of the bonding layer 16 and the support layer 12. As such, the risk of tearing of the surface of the support layer 12 is significantly mitigated providing a significantly improved bonding securement and seal between the mounting plate 4 and the bag 2. The force applied to pull the bag 2 away from the mounting plate 4 will not necessarily be a direct or normal force, but could instead be an indirect or shear force.

The resistance to tearing or peeling between the layers provided by the above described arrangement advantageously prevents separation or the layers, thereby avoiding escape of waste products from the bag and subsequent difficulties for the user.

It will be appreciated that in further embodiments various modifications to the specific arrangements described above and shown in the drawings may be made. For example the skin contact layer may in other embodiments be formed from a material other than hydrocolloid. In addition, while a two layered mounting plate arrangement is described, in other embodiments any suitable mounting plate arrangement may be provided having any number or flexible, rigid, planar and/or domed layers. While the bonding layer is preferably an annular layer of limited radial thickness having an inner edge located outwardly of the stomas port, in other embodiments it may extend entirely to the stoma port with none of the bag being thermally welded or otherwise bonded to the support disc. Furthermore, it should be appreciated that the term 'bonding layer' is not limiting and should be interpreted broadly as any layer that is bonded intermediate the bag and the mounting plate to both elements. The bonding layer does not have to itself be a bonding material. Rather the bonding layer may be a solid element and bonding between the bonding element and the bag and/or support layer may be effected by a separate adhesive and or any other suitable means. In addition, while the stress displacement element is preferably formed from a hot melt material, it may alternatively be provided as a preformed element such as solid plastic ring which is adhered to the intermediate layer by any suitable means for example a contact adhesive. It will also be appreciated that while the bonding layer is described as an annular disc, the bonding layer may be any suitable shape and configuration and is not limited to an annular arrangement.

Furthermore, while the invention is described for use in an ostomy pouch, it is also contemplated that the invention may be applied to joining other surfaces and material for other applications to mitigate damage by providing a stress off-set. Therefore, the invention may be considered in one embodiment to comprise a first material layer, a second material and a stress displacement element located between the first and second material layers and bonded to both. The region of bonding securement between the stress displacement element and the first layer has a first peripheral edge, and the region of bonding securement between the stress displacement element and the second layer has a second peripheral edge that is located inwardly of the first peripheral edge. As such, all aspects of the invention and the method of formation described above are not limited to the above described ostomy pouch application and may be applied individually or in any combination in line with the above embodiment.

Whilst endeavouring in the foregoing specification to draw attention to those features of the invention believed to be of particular importance it should be understood that the Applicant claims protection in respect of any patentable feature or combination of features hereinbefore referred to and/or shown in the drawings whether or not particular emphasis has been placed thereon.

The invention claimed is:

1. An ostomy pouch assembly comprising:
a receptacle for receiving material from a stoma of a person;
a mounting plate for securing the receptacle to a person's body, the mounting plate including a first layer having an outer surface configured to be bonded to a person's skin and an inner surface, and an intermediate layer located between the inner surface of the first layer and the receptacle; and
a stress displacement element located between the intermediate layer and the receptacle and bonded to both the receptacle and the intermediate layer;
wherein there is a first region of bonding securement between the stress displacement element and the intermediate layer, and a second region of bonding securement between the stress displacement element and the receptacle;
wherein the first region of bonding securement has a first peripheral edge, and the second region of bonding securement has a second peripheral edge that is located inwardly of the first peripheral edge; and
wherein the stress displacement element has an inner peripheral edge and a portion of the receptacle is directly bonded to the intermediate layer inwardly of the inner peripheral edge of the stress displacement element.

2. The ostomy pouch assembly according to claim 1, wherein the first layer is a hydrocolloid layer configured to be adhered to a person's skin.

3. The ostomy pouch assembly according to claim 1, wherein the intermediate layer is a foam material.

4. The ostomy pouch assembly according to claim 1, wherein the intermediate layer is bonded to the first layer.

5. The ostomy pouch assembly according to claim 1, wherein the first and intermediate layers comprise a common outermost peripheral edge that is located outwardly of the first and second peripheral edges.

6. The ostomy pouch assembly according to claim 1, wherein the receptacle is a bag formed from a flexible non-porous material.

7. The ostomy pouch assembly according to claim 1, wherein an aperture extends through both the first and intermediate layers defining a stoma port, and the stoma port is located inwardly of both the first and second peripheral edges.

8. The ostomy pouch assembly according to claim 7, wherein the stress displacement element is substantially annular defined between an element inner edge and the first peripheral edge, and wherein the second peripheral edge of the receptacle bonding region is located between the first peripheral edge and the element inner edge of the stress displacement element.

9. The ostomy pouch assembly according to claim 1, wherein the stress displacement element is a bonding material.

10. The ostomy pouch assembly according to claim 9, wherein the stress displacement element is a hot melt thermoplastic.

11. The ostomy pouch assembly according to claim 1, wherein the stress displacement element is a plastic member and is adhered to the intermediate layer and the receptacle.

12. The ostomy pouch according to claim 11, wherein the stress displacement element is a polymer disk coated with a pressure sensitive adhesive for bonding the disk to the intermediate layer and the receptacle.

13. The ostomy pouch assembly according to claim 8, wherein the receptacle is a bag and an aperture is defined in the bag which is aligned with the aperture extending through the first and intermediate layers to form part of the stoma port, the aperture defining an innermost edge of both the first and intermediate layers, and the bag is bonded directly to the intermediate layer between the element inner edge of the stress displacement element and the innermost edge defined by the aperture in the bag.

* * * * *